United States Patent
Vainshelboim et al.

(10) Patent No.: US 6,905,523 B2
(45) Date of Patent: Jun. 14, 2005

(54) HAIR COLOR APPLICATION USING CLUSTER-MODIFIED WATER

(75) Inventors: Alex Vainshelboim, Maple Grove, MN (US); Peter Matravers, Plymouth, MN (US); Asira Ostrovskaya, Bayside, NY (US); Kimberly Switlick, Wausau, WI (US); Julie Dachtera, Roseville, MN (US); Vasile Ionita-Manzatu, Old Bethpage, NY (US); George Cioca, Lake Grove, NY (US); Harvey Gedeon, Tenafly, NJ (US); Geoffrey Hawkins, Langhorne, PA (US); Michael Hayes, White Bear Lake, MN (US)

(73) Assignees: Aveda Corporation, Blaine, MN (US); Color Access, Inc., Melville, NY (US)

(*) Notice: Subject to any disclaimer, the term of this patent is extended or adjusted under 35 U.S.C. 154(b) by 112 days.

(21) Appl. No.: 10/387,777

(22) Filed: Mar. 13, 2003

(65) Prior Publication Data

US 2004/0177453 A1 Sep. 16, 2004

(51) Int. Cl.[7] ................................ A61K 7/13
(52) U.S. Cl. .................. 8/405; 8/401; 8/406; 8/425; 8/435; 8/444; 424/70.6
(58) Field of Search .................. 8/405, 401, 406, 8/425, 435, 444; 424/70.6

(56) References Cited

U.S. PATENT DOCUMENTS

| | | | |
|---|---|---|---|
| 5,711,950 A | 1/1998 | Lorenzen | 424/401 |
| 5,770,089 A | 6/1998 | Kubo | 210/661 |
| 5,846,397 A | 12/1998 | Manzatu et al. | 209/748 |
| 6,139,855 A | 10/2000 | Cioca et al. | 424/401 |
| 6,231,874 B1 | 5/2001 | Cioca et al. | 424/401 |
| 6,695,888 B2 * | 2/2004 | Bartolone et al. | 8/405 |

* cited by examiner

Primary Examiner—Mark Kopec
Assistant Examiner—Eisa Elhilo
(74) Attorney, Agent, or Firm—Dorene M. Price

(57) ABSTRACT

The invention relates to methods of coloring the hair with cluster-modified water and the ability to achieve enhanced color and conditioning for the hair that is color-treated. The cluster-modified water can be ionized water such as alkalinic or acidic water, or structured water such as I or S water. In addition, the cluster-modified water can be applied to the hair as a pre-saturating treatment and/or a post-saturating treatment relative to the hair color treatment process. Additional benefits of the present invention are the ability to minimize the use of harsh chemicals and dyes while still achieving an enriched color, and increased softness and smoothness to the color-treated hair. The present invention can also be used with mordanting salts. The present invention also includes a hair coloring kit including the cluster-modified water for post-saturating and/or pre-saturating the hair.

19 Claims, 2 Drawing Sheets

HAIR COLOR APPLICATION USING CLUSTER-MODIFIED WATER

FIELD OF THE INVENTION

The present invention relates to structured water and hair coloring systems for permanent, demi-permanent and semi-permanent hair color. In particular, the invention relates to the cluster-modified water and the ability to enhance color that is produced by dyeing the hair when clustered-modified water is included as part of the hair coloring application, and to condition the color-treated hair.

BACKGROUND OF THE INVENTION

The coloring of hair regardless of the reason is a process that must be applied correctly. In most cases, this means that the hair color is sharp and full from the first day of coloring. In addition, the consumer needs the hair color to last, at an absolute minimum of two weeks (i.e., colorfast). Thus, a dye must be colorfast to the everyday environmental exposure of hair, most notably shampooing, styling and sunlight. Colorfastness of a dye can vary widely. Therefore, dyes used in the coloring of hair are categorized as permanent, demi-permanent and semi-permanent. One of the most well known, and widely used coloring applications is the oxidative dyeing process. In this process, the dye is placed on the hair, and allowed to penetrate the hair and become oxidized, most typically with hydrogen peroxide to produce the desired color in the hair. The dye composition is comprised of two main components: primary and coupler. Both components are low molecular weight, which enables them to penetrate the hair and be polymerized in the presence of a base and hydrogen peroxide, to form a final, larger molecular weight dye. The chemical polymerization process in the presence of the base and the peroxide is a coupling or a condensation reaction. The base is an alkaline material that can be, for example, ammonium hydroxide, sodium hydroxide, potassium hydroxide, and calcium hydroxide. It is well established that use of these materials can to some extent be damaging to the hair.

In addition to dyes which provide permanent hair color, there are non-oxidative colorants which intentionally provide hair color that is more temporary. The fastness properties of these dyes are determined by ionic linkages, hydrogen bonding and van der Waals forces. These dyes are mostly used in the textile industry, where application procedures normally include the use of harsh chemicals and high temperatures. When used as hair dyes, however, the application of these dyes must be applied at much lower temperatures, and generally more mild conditions. Because of these compromises in application procedures, only a temporary coloring effect will be produced. Therefore, the color is expected to last only for several shampooing cycles. These types of dyes can be used either by themselves, or in conjunction with oxidative dyes to enhance vibrancy. To achieve good durability and/or permanent effect of hair coloring, harsh chemicals and conditions are necessary.

Thus, there is a need to produce a hair color application that provides vibrant and healthy long-lasting color with minimal use of a harsh environment. It has now surprisingly been discovered that cluster-modified water is capable of increasing the depth, intensity and durability of hair color, without the use of harsh chemicals. Cluster-modified water is anomalous to the specific chemical structure of commonly known regular water in that it contains three atoms, including two hydrogen and one oxygen, in a symmetrical triangular shape. However, while the chemical structure may be simple, the water molecule as a whole is very complicated. Due to its chemical structure, water molecules exhibit partially positive and negative sites forming a dipole moment. These sites are the hydrogen atoms which form the positive sites, and the oxygen atom which forms the negative site (due to the two lone pairs of electrons associated with oxygen). As a result of the dipole moment formed by the positive and negative sites, the water molecule is capable of a phenomenon known as hydrogen bonding. Thus, water molecules have a tendency towards forming hydrogen bonds between each other and this causes the water molecules to aggregate in various sizes. Depending on the treatment applied to water different types of cluster-modified waters can be produced. Examples of treated water, whereby ionic clusters contained within water are manipulated, are found in U.S. Pat. Nos. 6,139,855 and 5,711,950 describing I and S structured water.

The use of cluster-modified water in the process of coloring hair has been surprisingly found to give color-treated hair a higher intensity of color than with the same given amount of colorant on hair color-treated without cluster-modified water. In addition, the resulting color is more durable, and has a conditioned feel and lustrous look. These benefits are achieved with any type of cluster-modified water including electrically activated, magnetically clustered and any other structured water as a treatment in conjunction with any kind of hair color procedure. Previously, it has only been known to achieve these benefits with the use of harsh chemicals typically used in hair coloring and other industries such as oxidizers, reducing agents, alkalinic and acidic ingredients, aromatic carriers and elevated temperatures and pressures. Clustered-water application can provide the same improvements to the final color, without the additional use of the above-listed materials and/or environments.

SUMMARY OF THE INVENTION

The present invention relates to a system of hair coloring which enhances color intensity and conditions the color-treated hair with a simple application of cluster-modified water to the keratinous fiber. Most of the known procedures for increasing the depth and intensity of color, require opening the cuticle, and/or electro-chemical or chemical modification of the hair cuticle with the assistance of harsh chemicals. The present invention achieves these benefits based on the physical properties of less-aggregated water molecules, thus enabling the above-listed benefits to be obtained with decreased amounts of dye and harsh chemicals. Consequently, the system of the present invention is safer for the consumer to use, friendlier to the environment, and more economical to use. The hair coloring system comprises containers of at least one cluster-modified water, a hair coloring agent, and a shampoo.

Methods to increase color deposition on hair, especially gray hair has long been researched and still are only known to be based on the use harsh chemicals. However, the present invention has surprisingly discovered that a method of using cluster-modified water such as ionized water or structured water, as a pre-treatment and/or a post-treatment to hair fibers that undergoes a dye or tint application with a hair coloring agent has been successful in accomplishing increased conditioning of the color-treated hair as well as enhanced color.

The method of the present invention includes dyeing the keratinous fibers by soaking or saturating the hair with clustered-modified water. The hair is pre-soaked with the clustered-modified water for a period of time, before drying the hair. The normal hair-color treatment is applied using a hair coloring agent on the dry hair. Following the hair coloring, the method of the present invention also includes steps for soaking the hair for a second time with the cluster-modified water for a given period of time. After the post-soaking, the hair is dried and can be styled as usual. The treatment of the hair by pre-soaking and post-soaking can be done individually or collectively as a treatment. Any cluster-modified water, for example, structured water and ionized water, can have an effect on the condition and coloration of the hair. In addition, the present invention includes a hair coloring composition comprising cluster-modified water, at least one mordanting salt and at least one semi-permanent synthetic and/or natural dye.

DETAILED DESCRIPTION OF THE INVENTION

Figure 1:
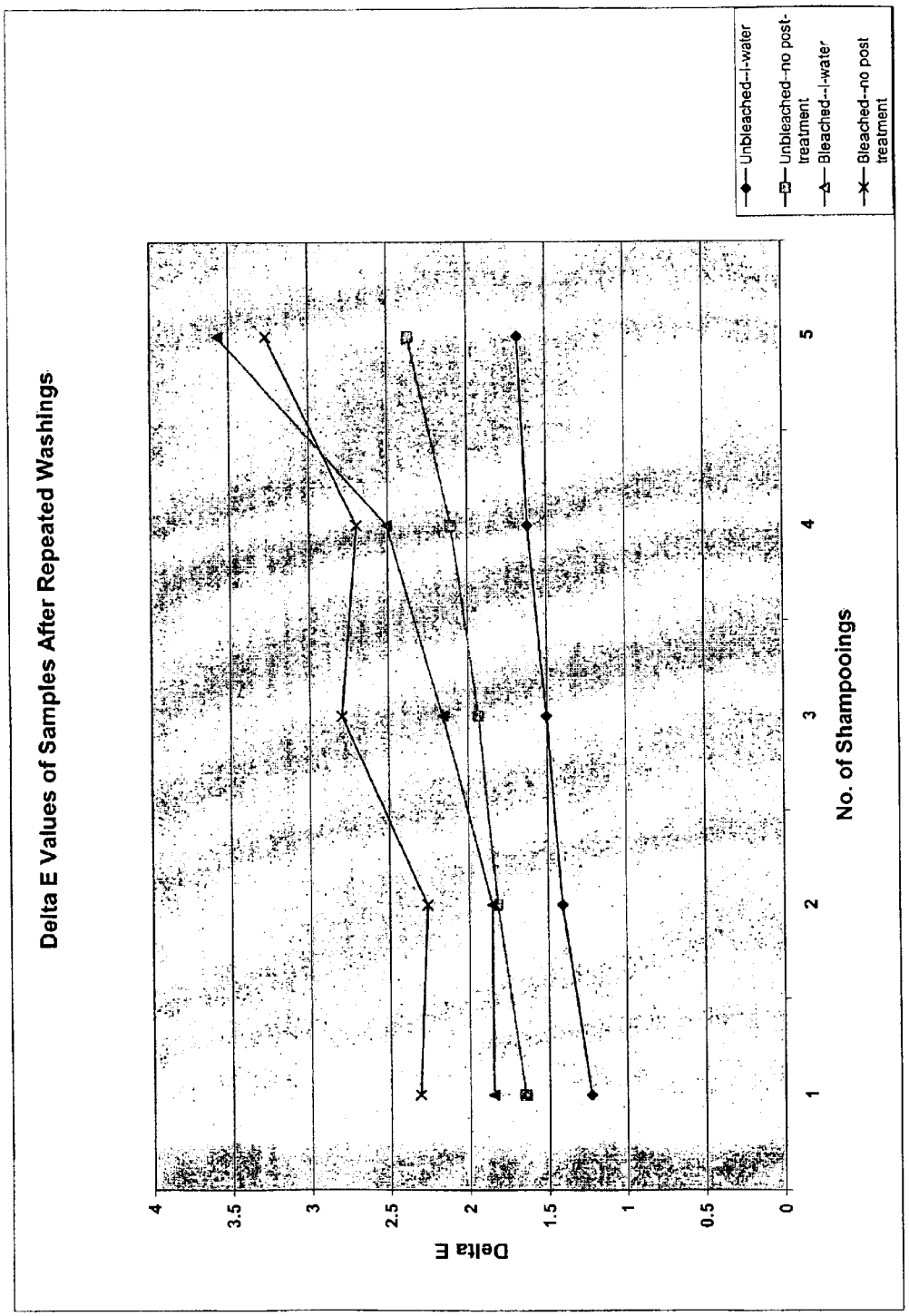
FIG. 1 is a chart illustrating the effect of the present invention using I water on bleached and unbleached hair after repeated washings (five) in causing an effect on color change after shampooing (ΔE), and consequently, improving the color fastness of hair dye and enhancing the hair color.

It has now been discovered that the color of color-treated hair can be intensified, and that the body and conditioning of the hair that is color-treated with a hair coloring agent can be enhanced by pre-soaking and/or post-soaking the keratinous fibers with a cluster-modified water. The cluster modification of the water can be, for example, a reduction in the size of water molecule clusters or separation of water molecules into hydroxyl and hydrogen ions, as in ionized water, or an organized structuring of ionic clusters as in structured water. As used herein cluster-modified water includes, but is not limited to, ionized water, and structured water. Thus, the scope of the present invention includes any water in which the clusters of water molecules, per se, or clusters of ions contained within the water are manipulated to modify the properties of the water. Specifically, structured water as used in the present specification refers to structured water described in, for example, U.S. Pat. Nos. 6,139,855 and 6,231,874. Structured water is made by treating feed water.

The feed water is an aqueous solution and has a C ($\mu$S/cm) of, for example, about 350 to about 550 and a pH of, for example, about 5.0 to about 7.5. The aqueous solution can be deionized water, distilled water or tap water. Specifically, the feed water solution is prepared with a cluster structure stabilizing ionic component of extremely small concentrations of cations and anions from materials such as for example, $CaCl_2$, $MgCl_2$, $Na_2SO_4$, $KH_2PO_4$, and $KNO_3$. The range of concentrations of ions in the ionic component can be, for example, $CaCl_2$ in an amount of about 5.00 to 10.00 mg/100 ml of the feed water, $MgCl_2$ in an amount of about 1.00 to 10.00 mg/100 ml, $Na_2SO_4$ in an amount of about 2.00 to 9.00 mg/100 ml, $KH_2PO_4$ in an amount of about 0.20 to about 2.00 mg/100 ml, and $KNO_3$ in an amount of about 0.90 to 9.00 mg/100 ml. For example, the ion content of the ionic component can be 11.00 mg/100 ml $CaCl_2$, 4.20 mg/100 ml $MgCl_2$, 5.00 mg/100 ml $Na_2SO_4$, 0.70 mg/100 ml $KH_2PO_4$, and 1.10 mg/100 ml $KNO_3$. The feed water has, for example, a pH of about 6.0 to 6.4 and a C ($\mu$S/cm) of about 470 to 520. The feed water can be optionally fed through a tourmaline filter at a flow rate of about 10 to 200 L/hour to reduce the surface tension of the feed water. A tourmaline filter suitable for lowering surface tension is described in U.S. Pat. No. 5,770,089, the contents of which are incorporated herein by reference.

After the desired feed water is prepared, it is processed in the structured water making device to make the structured water. The process of making structured water is described for example, in RO 88053 which describes a method for producing "B" or basic (S-type) water, and RO 88054 which discloses a method for making "A" or acid (I-type) water. Improvements in simultaneously making either of these types of water are further described in U.S. Pat. No. 5,846,397, the content of which is incorporated herein by reference. The structured water making device uses one or several serial structuring cells placed in a chemically inert parallelipipedic column made out of glass or plexiglass, for example. In a space for generating or producing the S water, the polarization and energy needed for binding water molecules, by hydrogen and hydroxyl bridges, in polymolecular aggregates (i.e., clusters) with radicals ($R_m^+$ stabilizing ions), is present as a result of the electrostatic field being about 80 to 120 V. Similarly, polymolecular aggregates (i.e., clusters) with radicals ($R_k^-$ stabilizing ions) are simultaneously formed to make I water, in a space for producing I water. The structured water of the present invention does not require special storage conditions or special packaging to protect it from destabilizing factors. Further, the cluster structure of structured water is very stable. The potential energy of the system of cluster structures in structured water as a whole is minimized.

Structured water contains electronegative and electropositive clusters of water molecules stabilized by ions. Each of these two types of clusters, present in water, is commonly referred to as "I water" and "S water". On the one hand, I water contains electronegative clusters of water molecules stabilized by ions which can be characterized as being $R_m^+ R_k^-(H^+)_n(H_2O)_l$, where k>>m, and conversely, on the other hand, S water contains electropositive clusters of water molecules stabilized by ions which can be characterized as being $R_k^- R_m^+ H_n^+(OH^-)_p(H_2O)_l$, where k<<m. In each case of I water and S water, $R_m^+$ ions mainly include, but are not limited to, $Ca^{+2}$, $Mg^{+2}$, $Na^+$, $K^+$ cations, and $R_k^-$ ions mainly include, but are not limited to, $Cl^-$, $H_2PO_4^-$, $SO_4^{-2}$ anions. The cluster structure of the structured water is very stable. While not wishing to be bound by any particular theory, it is believed that additional ions are introduced into the system of cluster structures by replacing the ion which stabilizes the structure with ions that have the same or similar ionic radius.

Ionized water as used herein refers specifically to water that has been processed to separate the water molecule into its ions (i.e., $H^+$, and $OH^-$) or processed with a water ionizer such as, for example, Ionice SDM-2000 Water Ionizer which is commercially available, to reduce the size of natural clusters of water molecules bonded by hydrogen bonding. The ionizer produces alkalinic water (e.g., pH of about 9 to 12) and acidic water (e.g., pH of about 2 to 6).

Any cluster-modified water can be used to pre-soak and/or post-soak the hair. When pre-soaking or post-soaking the hair, the cluster-modified water can be sprayed onto the hair using a spray bottle or by any other means of application to saturate the hair. The amount of cluster-modified water used to saturate the hair will vary depending on the quantity of hair being soaked. The soaked hair is allowed to set for a period of time. The setting time is about 30 seconds to about 15 minutes, preferably 1 to 10 minutes, and more preferably 2 to 8 minutes. To dry the hair, it can be blown dry with a hair dryer using low heat, medium airflow setting or towel dried. After soaking the hair a second time, the colored and post-soaked hair can be blown dry or towel dried, and styled as usual.

Thus, preferably, for example, S water is applied as a pre-soak to intensify the color of the hair. The color is slightly richer and/or warmer in tone without changing the level of color. Structured water such as I water is applied as a post-soak to improve the body and condition the hair. The improved body and condition is defined by an improved texture (i.e., softer), bounce and volume of the hair. These conditions are similar to a conditioning treatment and are long lasting, for example, for at least one or two days. Increased color intensity lasts for several washings indicating an increased colorfastness. The term colorfastness means that the color treated hair exhibits a reduction in color fading after washing.

Any dye or tint can be used with the present invention to color the hair permanently, semi-permanently, demi-permanently or temporarily. Thus, the coloring agent can be a dye that is oxidative or non-oxidative. However, in one embodiment of the present invention, a natural non-oxidative hair dye is used and the cluster-modified water is combined with a mordanting salt to further enhance the color fastness. The natural dye is a coloring compound that is found within and/or derived from naturally occurring materials such as for example, but not limited to, plants, roots, spores, and fungi. In this embodiment, the hair fiber is pre-soaked and/or post-soaked with a combination of the cluster-modified water and the mordanting salt. Many mordants are commonly known in the art and include, but are not limited to polyvalent metal ions. The mordant, present in the cluster-modified water, chelates with the dye to form a large metal-dye complex. The combination of the mordanting salt and the cluster-modified water can be applied to the hair at any time, e.g., prior or after dyeing. Before the complex is formed with the mordant, a dye can more readily diffuse into the hair fiber because it is a relatively small sized molecule. After the dye-mordant complex forms, it is much larger in size than the original dye molecule, and preferentially can remain inside the hair fiber. Surprisingly, this effect is found with the cluster-modified water of the present invention. While not wishing to be bound by any particular theory, it is believed that the formation of the dye-mordant complex is fortified by the ions that stabilize the cluster structures.

The mordants are polyvalent metal ions (having a valence of at least 2), particularly cations such as magnesium, aluminum, chromium, copper, tin, and the like. Examples of specific mordants, include, but are not limited to, aluminum potassium sulfate, aluminum ammonium sulfate, magnesium sulfate, aluminum citrate, aluminum lactate, and aluminum acetate, or mixtures thereof. The mordanting salts are present in an amount of about 0.1 to about 15.0 percent by weight of the composition; and preferably about 5 to 15 percent; and most preferably about 10 to 15 percent.

In addition, any shampoo can be used to wash the hair. The present invention also includes methods of improving the condition of the hair, and enhancing the color of the hair that undergoes a color treatment. Further, the present invention can also be applied in a hair coloring system. The hair coloring system can be in the form of a kit that includes at least one container of cluster-modified water. In addition, the kit includes a hair coloring agent, and shampoo.

The following non-limiting examples illustrate the invention.

EXAMPLES

Example I

Enriching Hair Color with Ionized Water

A study to test the increased intensity of color on hair, involves an evaluation of three samples of hair treated as follows: One sample (1Dc) is color treated with Aveda Full Spectrum™ Permanent Hair Color (red-orange R/O 135728; 20 volume catalyst; 30 minute application time), rinsed with tap water and blown dry. Hair is moistened with tap water before applying color treatment. A second sample (3Dc) is moistened with alkalinic ionic ($OH^-$) water for about 5 minutes, color treated, rinsed with tap water, conditioned with acidic ($H^+$) ionic water, and blown dry. A third sample (5Dc) is moistened with alkalinic ionic ($OH^-$) water for about 5 minutes, blown dry, color treated, rinsed with tap water, and conditioned with acidic ionic ($H^+$) water. The 3Dc sample appears to have the darkest and most vibrant color of the three samples indicating that ionized water enriches the intensity of the color of color-treated hair.

Example II

Enhancement of Hair Color Using I-Water with Acid Dyes

This example includes evaluation of cluster-modified, and specifically of I-water as a post-treatment. This study focuses solely on acid dyes; no oxidative systems are evaluated.

Figure 2:
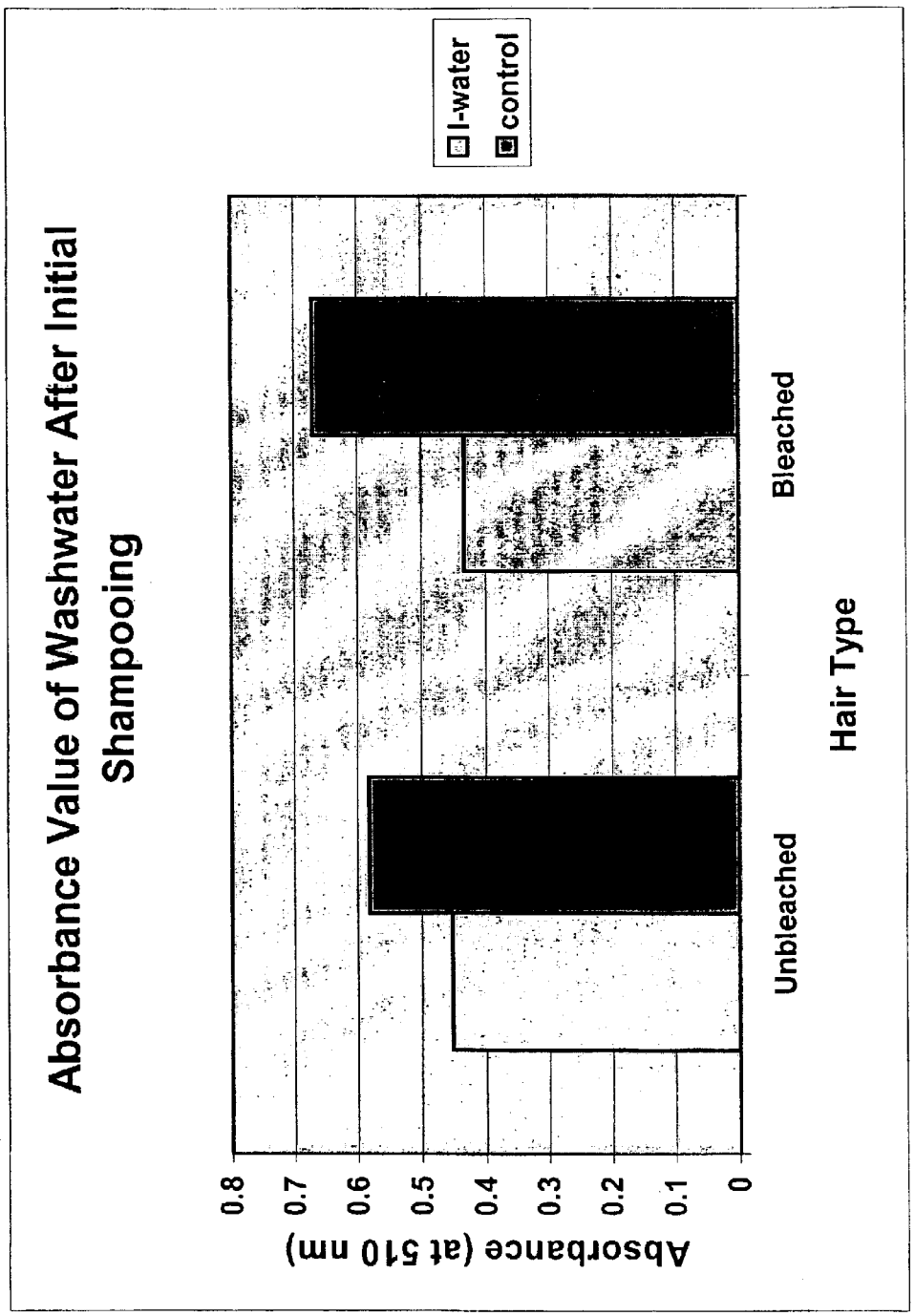
FIG. 2 is a chart depicting the absorbance value of washwater after initial shampooing on unbleached and bleached hair treated with I water and indicating an improvement in the color fastness and the enhancement of hair color.

All tresses are dyed using a red-orange (R/O) acid dye paste similar in hue to Example I. Dyes included in this paste are C.I. Acid Red 33 and C.I. Acid Orange 7. Paste is brushed into hair using applicator brush, and then placed in an oven for 20 minutes at 40° C. Hair tresses are then rinsed under warm running tap water until clear. I-water is evaluated as a post-treatment to hair coloration. Experiment is conducted on both unbleached and bleached Level 5 hair (light brown color on a scale of 1 to 10 with 1 being black and 10 being light blonde). Post-treatments are applied by spraying and subsequent combing. Samples are thoroughly blow-dried using high heat. Samples are evaluated for the following properties: color change after shampooing ($\Delta E$), and residual dye present in shampoo washwater, (absorbance measurements at 510 nm of water from tresses washed in a 5% solution of Aveda All Sensitive™ shampoo). Lower delta E values indicate less color change. Lower absorbance value indicates less residual dye in shampoo bath. FIGS. 1 and 2, respectively, illustrate the differences found between treatments.

In order to determine significance between treatments, paired t-tests, based on 95% confidence levels are performed on color change of hair after shampooing, over five shampoo treatments and residual dye in shampoo bath after initial shampooing. Significantly less color change ($\Delta E$) is noted with I-water hair after initial shampooing for both bleached and unbleached hair. This difference continues to be significant after 5 shampooings for unbleached hair, indicative of superior color retention in I-water treated samples after shampooing. There is significantly less residual dye found in shampoo washwater for I-water post-treated samples after the initial shampooing, for both bleached and unbleached hair, meaning the I-water treated samples have superior washfastness than controls. The above measurements establish the benefits provided by I-water of the present invention; namely, improved washfastness and color stability (i.e., color fastness).

Example III

Enriching Color with Structured Water and Permanent Hair Color

Half-head evaluations are performed on qualified test subjects. Activated water is applied to the left half of heads before, during or after standard hair color applications and tap water is used on the right half of heads in standard hair coloring procedures. Aveda Full Spectrum™ Permanent or Deposit Only hair color is used for all subjects. The average pH level of water with anion/alkaline rich clusters was 11. The average pH level of water with cation/acid rich clusters is 3. Subjects are evaluated for color intensity, and scored on a nine-point scale. For pre-color activated alkaline water/ post-color activated acidic water hair color processing, mean score analyses with Statistica using the t-test for dependent samples at the 95% confidence interval, indicates a significantly more intense color in comparison to the hair using standard tap water color processing.

What we claim is:

1. A method of dyeing keratinous fibers comprising the steps of:
   a) pre-soaking the fibers with cluster-modified water, comprising a combination of I and S water resulting from feed water with a conductivity of about 350 to 550 and pH of about 5.0 to about 7.5 and
   b) treating the fibers with a hair coloring agent.

2. The method of claim 1 further comprising the step of removing the cluster-modified water by drying the hair.

3. The method of claim 1 wherein the cluster-modified water is ionized water or structured water.

4. The method of claim 3 further comprising the step of combining the cluster-modified water with at least one mordanting salt.

5. The method of claim 3 wherein the structured water further comprises electronegative aggregates of water molecules forming I water or electropositive aggregates of water molecules forming S water.

6. The method of claim 3 wherein the ionized water further comprises alkalinic water or acidic water.

7. A method of dyeing keratinous fibers comprising the steps of:
   a) treating the fibers with a hair coloring agent; and
   b) post-soaking the fibers with cluster-modified water comprising a combination of I and S water resulting from feed water with a conductivity of about 350 to 550 and pH of about 5.0 to about 7.5.

8. The method of claim 7 further comprising the step of combining the cluster-modified water with at least one mordanting salt.

9. A method of dyeing keratinous fibers comprising the steps of:
   a) pre-soaking the fibers with cluster-modified water comprising a combination of I and S water resulting from feed water with a conductive of 350 to 550 and pH of about 5.0 to about 7.5;
   b) removing the cluster-modified water from the fibers;
   c) treating the fibers with a hair coloring agent; and
   d) post-soaking the fibers with cluster-modified water.

10. The method of claim 9 wherein the steps of pre-soaking and post-soaking the fibers further comprise the step of combining the cluster-modified water with at least one mordanting salt.

11. The method of enhancing the color of color-treated hair comprising the steps of claim 1.

12. The method of increasing the body and condition of dyed hair comprising the steps of claim 7.

13. The method of claim 12 wherein the cluster-modified water is structured water of electronegative aggregates of water molecules forming I water.

14. The method of claim 12 wherein the cluster-modified water is ionized water of acidic water.

15. A hair coloring system comprising containers of at least one cluster-modified water, comprising a combination of I and S water resulting from feed water with a conductivity of about 350 to 550 and pH of about 5.0 to about 7.5, a hair coloring agent, and a shampoo.

16. The hair coloring system of claim 15 wherein said cluster-modified water is ionized water or structured water.

17. The hair coloring system of claim 16 wherein the ionized water is acidic or alkalinic.

18. The hair coloring system of claim 16 wherein the structured water is electronegative aggregates of water molecules forming I water or electropositive aggregates of water molecules forming S water.

19. A hair coloring composition comprising cluster-modified water comprising a combination of I and S water resulting from feed water with a conductivity of about 350 to 550 and pH of about 5.0 to about 7.5, a least one mordanting salt, and at least one semi-permanent synthetic and/or natural dye.

* * * * *